United States Patent [19]

Hamilton

[11] Patent Number: 5,314,669
[45] Date of Patent: May 24, 1994

[54] METHOD AND APPARATUS FOR DISPENSING A SCENT INTO THE AIR

[76] Inventor: Randy Hamilton, 8621 S. Kenwood La., Tempe, Ariz. 85284

[21] Appl. No.: 898,483

[22] Filed: Jun. 15, 1992

[51] Int. Cl.⁵ .............................................. A61L 9/03
[52] U.S. Cl. .................................. 422/305; 422/123; 239/52; 239/58; 239/59
[58] Field of Search ........................ 239/58, 59, 52; 422/123, 305, 306, 4, 5; 220/253; D23/369

[56] References Cited

U.S. PATENT DOCUMENTS

| | | | |
|---|---|---|---|
| D. 321,050 | 10/1991 | Weick | D23/369 |
| 2,555,047 | 5/1951 | Logue | 239/58 |
| 2,778,678 | 1/1957 | Shields et al. | 422/124 |
| 3,419,217 | 12/1968 | White et al. | 239/58 |
| 3,722,182 | 3/1973 | Gilbertson | 55/124 |
| 3,797,742 | 3/1974 | Clark et al. | 239/57 |
| 4,200,229 | 4/1980 | Spector | 239/57 |
| 4,258,874 | 3/1981 | Webinger et al. | 229/23 BT |
| 4,301,095 | 11/1981 | Mettler et al. | 261/30 |
| 4,572,376 | 2/1986 | Wrennall | |
| 4,813,344 | 3/1989 | Greif | 454/156 |
| 4,903,584 | 2/1990 | Styles | 454/284 |
| 4,913,034 | 4/1990 | Ripple et al. | 454/157 |
| 4,950,457 | 8/1990 | Weick | 422/123 |
| 4,959,087 | 9/1990 | Kappernaros | 55/279 |
| 5,050,798 | 9/1991 | Sullivan | 239/58 |
| 5,163,616 | 11/1992 | Bernaducci et al. | 239/35 |

Primary Examiner—Timothy M. McMahon
Attorney, Agent, or Firm—David G. Rosenbaum

[57] ABSTRACT

A new and improved method and apparatus are presented for freshening the air. The device comprises an inner cylindrical member with vents, with a retaining carriage which is capable of housing at least two separate and distinct scented media, and an outer cylindrical member with vents. The inner cylindrical member is concentrically retained within the outer cylindrical member and can be rotated to achieve different alignments of the vents in the inner and outer cylindrical members. The device enables two or more separate and distinct scented media to interface with the air and thereby disperse their scent either in the alternative, thereby enabling the dispersal of different scents without changing the media within the retaining carriage, or at the same time, thereby creating a new and distinct scent due to the multiple air interface of the scented media.

6 Claims, 3 Drawing Sheets

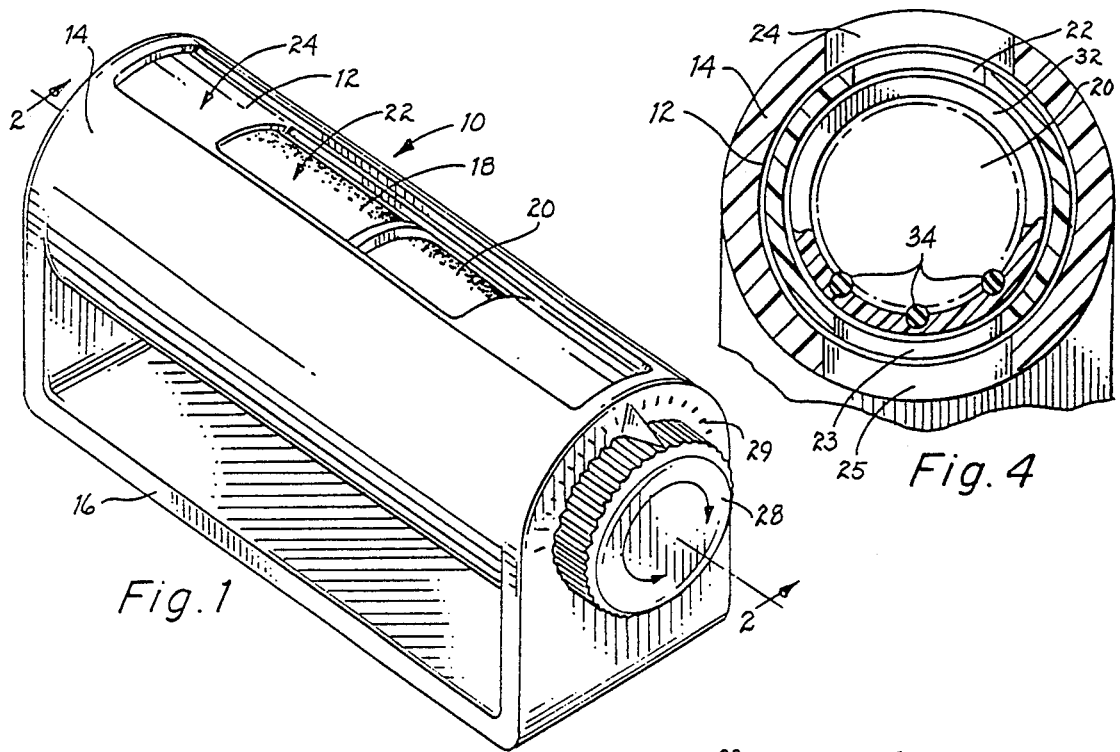
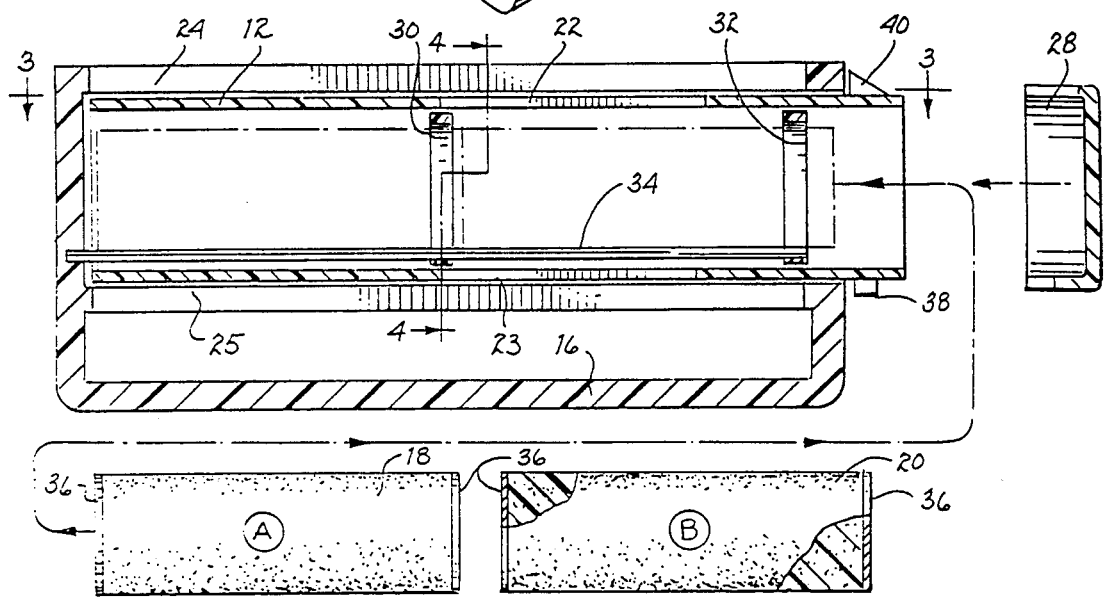
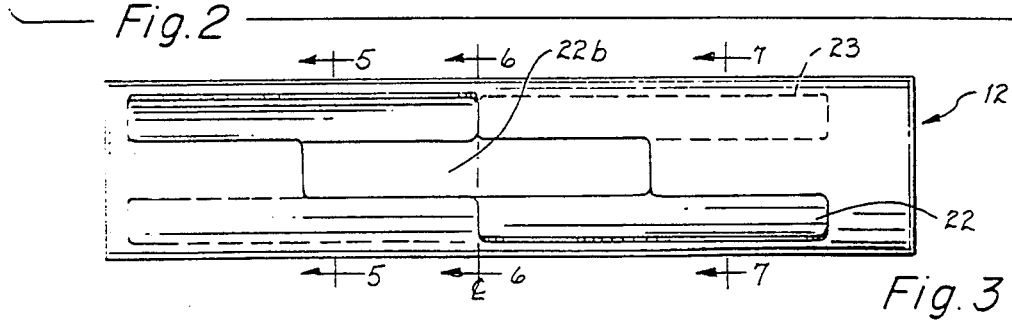

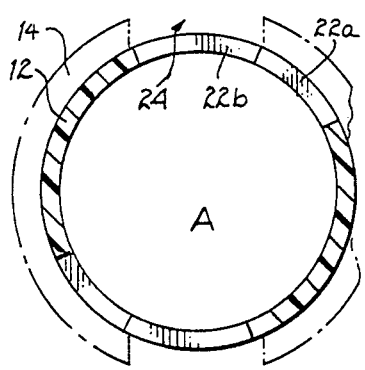 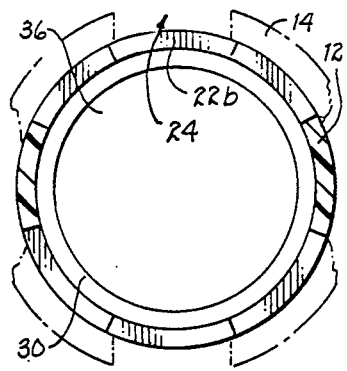 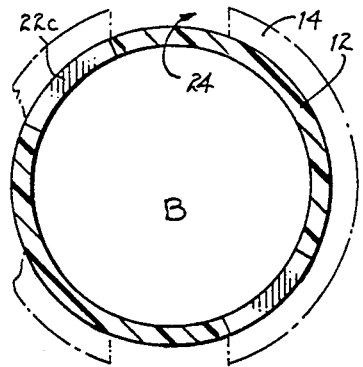
Fig.5   Fig.6   Fig.7
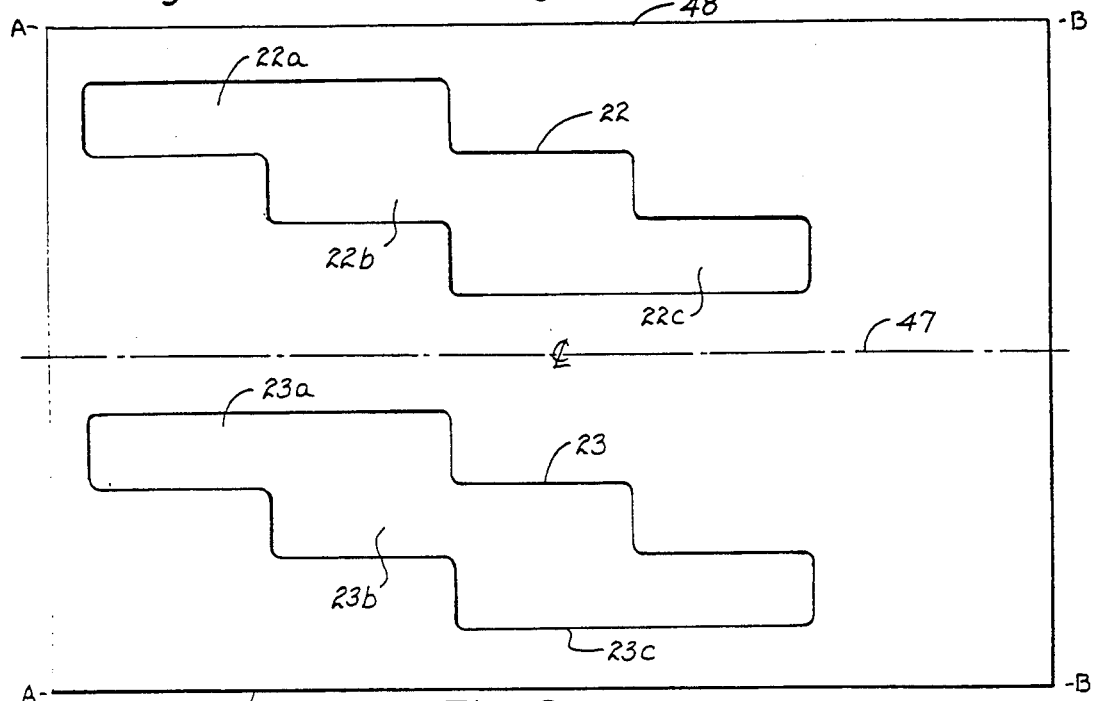
Fig.8
Fig.9A
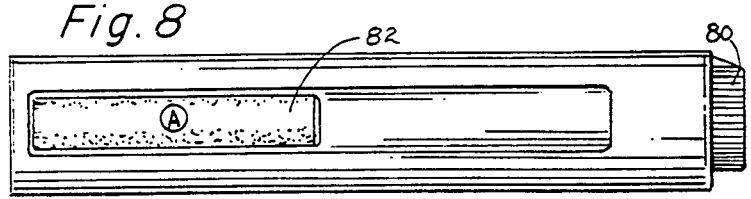
Fig.9B
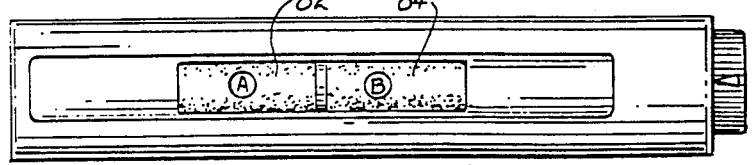
Fig.9C

METHOD AND APPARATUS FOR DISPENSING A SCENT INTO THE AIR

BACKGROUND OF THE INVENTION

The present invention relates generally to an air freshening device which can also be used as an automobile air freshener. More particularly, the present invention relates to an air freshening device designed to accommodate two different scent bearing media, thereby enabling a user to choose between individual alternative scents or blended scents without changing an entire media cartridge contained in the device.

Various types of air freshening devices have been designed. U.S. Pat. No. 4,950,457 describes a device with two concentrically disposed cylindrical tubes which surround an evaporative chamber holding an active liquid. Slits are present in the outer cylinder to allow for the release of the active liquid. The active liquid is adsorbed onto pads loaded into changeable cartridges. U.S. Pat. No. 4,258,874 describes a two part paperboard container with adjustable vents in each of inner and outer concentrically and co-axially aligned conical members which are frictionally engaged upon one another. A sublimable material, whose process of sublimation is regulated by the adjustable vents, is placed within the inner tubular member. U.S. Pat. No. 4,200,229 describes an aroma-dispensing cartridge and holder assembly in which a replaceable bottle, filled with a liquid scent, is closed by a suction pump attached to a stopper. The pump includes a flexible pipe extending into the bottle which draws liquid out when a spring-biased hollow plunger in the pump is activated. U.S. Pat. No. 3,797,742 describes an air-treating device with a hollow container dispenser, containing a plurality of apertures, which holds a stack of sealed packets each containing a solid air treating agent. The individually sealed packets are individually removed, opened, and placed at the top of the container, near the apertures, to engage the air treating device. U.S. Pat. No. 4,813,344 describes a deodorizer containing dispenser which engages with an automobile airduct. The device has openings in its top surface and grooved sides to allow exposure of the deodorizing agent to an air flow emanating from the air duct.

Additionally, other types of air freshening devices have been invented for use primarily in automobiles. U.S. Pat. Nos. 2,778,678, 3,772,182, and 4,913,034 disclose various deodorant dispensing devices which are designed for positioning in various locations of an automobile in order to employ air movement through the automobile's air duct system to release the deodorant or scent.

SUMMARY OF THE INVENTION

It is an object of the present invention to provide a new and improved air freshening device. It is also an object of the present invention to provide a new and improved air freshening device wherein the inner chamber is sub-divided into two sub-chambers which retain discrete containers of scented media to enable alternative individual or mixed scent selection without completely replacing a scent container. It is a further object of the present invention to provide an air freshening device from which two different and distinct scents can be released at the same time upon exposure to an air flow, thereby creating a third new and distinct scent resulting from the combination or mixture of the first two scents in the surrounding air.

Accordingly, the inventive air freshening device consists generally of concentric outer and inner cylindrical members with a friction interface between them, and may include a carriage located within the inner cylindrical member for holding scent filled media containers. Each of the cylindrical members consists of a first end, a second end and a lumen. Scent filled media containers are inserted into the carriage within the inner cylindrical member which is, in turn, inserted into the outer cylindrical member. Alternatively, the scent filled media containers may be inserted directly into the lumen of the inner cylindrical member. An end portion of the inner cylindrical member protrudes from the outer cylindrical member and serves as a rotatable handle. Both inner and outer cylindrical members have longitudinal vents which when aligned expose the scented media to an air flow and when out of alignment seal the scented media and inner cylindrical member. The device is further designed so that the carriage within the lumen of the inner cylindrical member is capable of housing two separate containers of scented media. The carriage, which consists of at least one rod member and at least one ring member, prevents the two differently scented media from mixing.

The objects and advantages of this invention will appear more fully from the following more detailed description of the preferred embodiment of the invention made in conjunction with the accompanying drawings.

BRIEF DESCRIPTION OF THE DRAWINGS

FIG. 1 is a perspective view of one embodiment of an air freshening device in accordance with the present invention.

FIG. 2 is a cross-sectional exploded view taken along line 2—2 of FIG. 1.

FIG. 3 is a top elevational view of the inner cylindrical chamber of the present invention taken along line 3—3 of FIG. 2.

FIG. 4 is a cross-sectional view taken along line 4—4 of FIG. 2.

FIG. 5 is a cross-sectional view taken along line 5—5 of FIG. 3.

FIG. 6 is a cross-sectional view taken along line 6—6 of FIG. 3.

FIG. 7 is a cross-sectional view taken along line 7—7 of FIG. 3.

FIG. 8 is a plan view of an unrolled first preferred embodiment of the inner cylindrical member of an air freshening device in accordance with the present invention.

FIG. 9A is a top elevational view of an air freshening device in accordance with the present invention.

FIG. 9B is a top elevational view of an air freshening device in accordance with the present invention.

FIG. 9C is a top elevational view of an air freshening device in accordance with the present invention.

DETAILED DESCRIPTION OF THE PREFERRED EMBODIMENT

Figure 10:
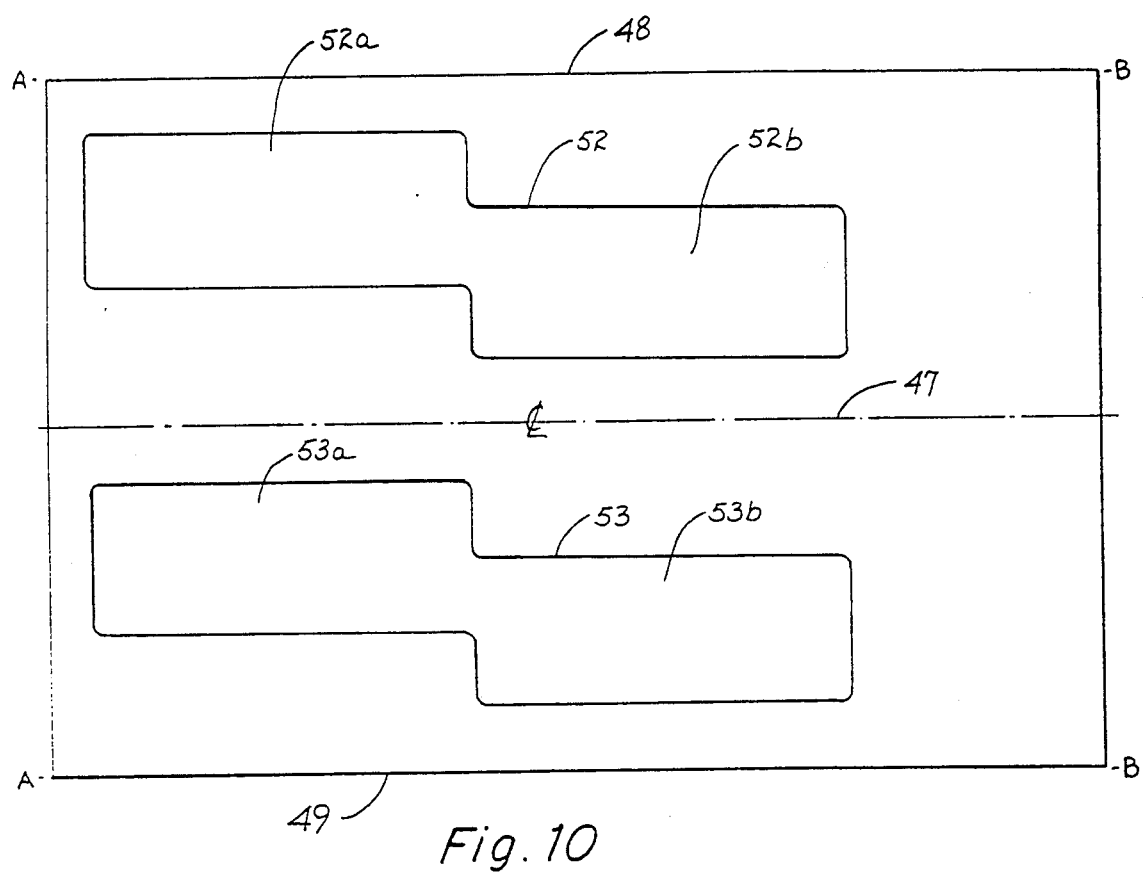
FIG. 10 is a plan view of a second preferred embodiment illustrating an unrolled inner cylindrical member of an air freshening device in accordance with the present invention.

FIG. 1 illustrates the air freshening device 10 of the present invention. Generally, the air freshening device 10 consists of a rotatable inner cylindrical member 12 and a fixed outer cylindrical member 14 which further comprises a base 16 which supports both inner and outer cylindrical members 12,14. Base member 16 can be attached to a surface, for example the dashboard of a car, by using a hook and loop material such as "VELCRO", adhesive, mechanical, or a similar means of attachment. Inner cylindrical member 12 is capable of housing two discrete containers of scented media 18,20 which are exposed through longitudinal opening 22 in inner cylindrical member 12 and longitudinal opening 24 in outer cylindrical member 14. As illustrated in FIG. 2, inner cylindrical member 12 extends beyond outer cylindrical member 14 and base support 16 to form protrusion 26. Dial 28 is attached to protrusion 26 to enable a user to adjust the alignment of the longitudinal openings 22,24 in inner and outer cylindrical members 12,14 by rotating the dial 28 to align a pointer or indicator with positional indicia 29 marked on the base 16 adjacent the dial 28.

With reference to FIG. 2, there is illustrated a cross-sectional view of air freshening device 10 with scented media containers 18,20 shown exploded. Both inner and outer cylindrical members 12, 14 contain two separate vents. Top vent 22 and bottom vent 23 are present in inner cylindrical member 12, while top vent 24 and bottom vent 25 are present in outer cylindrical member 14. An optional retaining carriage shown in phantom may be provided within inner cylindrical member 12 to hold the scented media containers in place. One embodiment of the retaining carriage comprises a first ring member 30 and a second ring member 32 which are connected by rods 34 which are in turn anchored in inner cylindrical member 12 and outer cylindrical member 14. A cross section of the retaining carriage is illustrated in FIG. 4. In FIG. 4, rods 34 are embedded in or attached to second ring member 32 which is located within inner cylindrical member 12. Other means for holding the scented media containers in place, such as four rods positioned to form a cage around the media containers, or a molded plastic carriage with large openings for the scented media, etc., are clearly contemplated by the present invention. Alternatively, scented media containers 18,20 may be placed within the inner cylindrical member 12 and frictionally retained within said member 12 such that they are substantially stationary within the member 12 thereby eliminating the need for a retaining carriage.

With further reference to FIG. 2, a first container 18 containing scented media A is placed inside the retaining carriage within inner cylindrical member 12 followed by a second container 20 containing scented media B Scented media containers 18,20 comprise end pieces 36 which function as physical barriers to prevent the scented media from mixing. In addition, end pieces 36 mate underneath first ring member 30 which further functions to seal and separate the scented media. Those skilled in the art will appreciate that end pieces 36 may be comprised of any substance or substances which will prevent scented media A and scented media B from mixing, such as plastic, plastic-coated paper, plastic-coated cardboard, etc. In addition, the scented media in the containers 18,20 may exist in the form of a gel, beads, fiber, plastic matrix, etc., or any other variety of forms which are capable of absorbing a scent as is known in the art.

As previously described, inner cylindrical member 12 fits concentrically inside outer cylindrical member 14 and extends beyond the end of outer cylindrical member 14. Clip members 38,40 assist in locking removable dial 28 in place. Clip member 40 also functions as an indicator for removable dial 28. Base member 16 is attached to outer cylindrical member 14 to provide a means for the easy attachment of air freshening device 10 to various surfaces. Base member 16 and outer cylindrical member 14 may be made as separate pieces which can be connected, or may be molded as an integral unit. Other embodiments of base member 16, such as a clipping means for snapping outer cylindrical member 14 into place, or a hooking means for hanging outer cylindrical member 14 in place, are also anticipated by the present invention.

A diagram of an unrolled first preferred embodiment of inner cylindrical member 12 is shown in FIG. 8. Two step-shaped vents 22, 23 of identical shape and size are cut into the top and bottom halves of unrolled inner cylindrical member 12, which are separated by center line 47. The step-shaped vents are defined by three generally rectangular staggered openings adjacent one another in a step-like formation. Accordingly, as shown in FIG. 8, vent 22 is defined by rectangular shaped openings 22a, 22b, 22c, and vent 23 is defined by rectangular openings 23a, 23b, 23c. Top edge 48 of unrolled cylindrical member 12 is attached to bottom edge 49 of unrolled cylindrical member 12 to form a cylinder with top and bottom vents which are mirror images of one another as shown in FIG. 3.

A diagram of a second preferred embodiment of an unrolled inner cylindrical member 12 is illustrated in FIG. 10. As in the first preferred embodiment, two step-shaped vents 52, 53 of identical shape and size are cut into the top and bottom halves of unrolled inner cylindrical member 12, which are separated by center line 47. However, in this preferred embodiment, the step-shaped vents are defined by two generally rectangular staggered openings adjacent one another in a step-like formation. Accordingly, as shown in FIG. 10, vent 52 is defined by rectangular shaped openings 52a and 52b, and vent 53 is defined by rectangular openings 53a and 53b. As in the first preferred embodiment, top edge 48 of unrolled cylindrical member 12 is attached to bottom edge 49 of unrolled cylindrical member 12 to form a cylinder with top and bottom vents which are mirror images of one another.

FIG. 3 illustrates a top elevational view of the first preferred embodiment of inner cylindrical member 12. Top vent 22 is represented by continuous lines while bottom vent 23 is represented in phantom where bottom vent 23 does not overlap with top vent 22. Opening 22b represents that part of top vent 22b and bottom vent 23b which are in direct alignment with one another and coincide to form an opening of the same shape and size through both upper and lower surfaces of the inner cylindrical member 12. Those skilled in the art will appreciate that the inventive device contemplates any vents which are shaped and designed to enable dual and alternate alignment with two or more different and distinct medias. The step-shaped vents merely exemplify one preferred embodiment.

In a cross-sectional view of the preferred embodiment of the present invention as illustrated in FIG. 4, the first preferred embodiment of inner cylindrical member 12, with top vent 22 and bottom vent 23, is housed inside of outer cylindrical member 14, with top vent 24 and bottom vent 25. As previously discussed, the optional retaining carriage, comprising ring member 32 and rods 34, fits inside inner cylindrical member 12 to function as a means for holding scented media container 20. This cross-sectional representation of the present invention shows inner cylindrical member 12 rotated to a position in which top and bottom vents 22, 23 of inner cylindrical member 12 are in direct alignment with top and bottom vents 24, 25 of outer cylindrical member 14, respectively. This alignment of the inner cylindrical member 12 and outer cylindrical member 14 allows scented media container 20 to interface with air passing through top vents 22, 24 and bottom vents 23, 25, thereby emitting a scent into the surrounding air. Alternatively, the inventive air freshener device may be placed in an air duct or in front of an air duct or register in order to take advantage of the air flow through the vent. In this instance, air would flow through bottom vents 54, 60, into the scented media, and out through top vents 53, 58. This type of forced air flow would result in an increased dispersal of the scented media.

FIGS. 5–7 represent cross-sectional views taken at various points along the horizontal axis device 10 where rectangular openings 22b and 23b of the first preferred embodiment of inner cylindrical member 12 are in direct alignment with the rectangular shaped vents 24, 25 of the outer cylindrical member 14. FIG. 5 illustrates a cross-sectional view taken along line 5—5 of FIG. 3 as if the inner cylindrical member 12 depicted in FIG. 3 were fitted inside outer cylindrical member 14 in accordance with the above-described alignment. The cross-section in FIG. 5 cuts through rectangular openings 22a, 22b of step-shaped top vent 22 in inner cylindrical member 12. Only rectangular opening 22b of step-shaped top vent 22 is in alignment with vent 24 in outer cylindrical member 14. Scented media A contained within inner cylindrical member 12 interfaces with air through rectangular opening 22b in top vent 22 of inner cylindrical member 12 and top vent 24 in outer cylindrical member 14. Rectangular opening 22a of step-shaped top vent 22 in inner cylindrical member 12 is sealed against the inner wall of outer cylindrical member 14 thereby cutting off the air interface with media A through opening 22b.

FIG. 6 illustrates a cross-sectional view taken along line 6—6 of FIG. 3 which illustrates the positioning of rectangular opening 22b of step-shaped top vent 22 of inner cylindrical member 12. End pieces 36 of scented media containers 18, 20 are sealed underneath first ring member 30 of the previously described retaining carriage. First ring member 30 is exposed to an air interface through rectangular opening 22b in top vent 22 of inner cylindrical member 12 and top vent 24 in outer cylindrical member 14.

A cross-sectional view taken along line 7—7 of FIG. 3, which cuts through only one rectangular opening 22c of step-shaped top vent 22 in inner cylindrical member 12, is shown in FIG. 7. Scented media B contained in this part of the inventive device, that part being represented by the cross-section, is blocked from interfacing with air by inner cylindrical member 12 which forms a barrier between top vent 24, in outer cylindrical member 14, and scented media B. As previously noted, the top and bottom vents of inner cylindrical member 12, which are shown in FIGS. 5–7, are identical in size and shape and depict exact mirror images of one another in every rotatable position of inner cylindrical member 12. The relationship between the bottom vents of both inner and outer cylindrical members in FIG. 5, FIG. 6, and FIG. 7, is the same as that described between the top vents of both inner and outer cylindrical member in FIG. 5, FIG. 6, and FIG. 7, respectively.

FIGS. 9A, 9B, and 9C represent top elevational views of the inventive device with the first preferred embodiment of inner cylindrical member 12 at different rotatable positions. In FIG. 9A, inner cylindrical member 12 is rotated by dial 80 to a position such that only scented media A 82 is able to interface with the air through the vents in both inner and outer cylindrical members. FIG. 9B illustrates the position of inner cylindrical member 12 which allows both scented medias A and B 82, 84 to interface with the air through the aligned vents of the inner and outer cylindrical members. FIG. 9C shows inner cylindrical member 12 in a position that enables only scented media B 84 to gain access to an air interface through inner and outer cylindrical member vents.

Those skilled in the art will understand and appreciate that air inner and outer cylindrical members 12, 14, base 16, and dial 28 may be made of any suitable plastic material, such as polyvinylchloride, polycarbonate, or other such plastic materials which may be molded and die cut as is known in the art. Furthermore, it is desirable, according to the best mode contemplated by the invention, to have ring members 30, 32 made of flexible plastic, rubber, or any other suitable material that will provide a flexible seal when scented media containers 18, 20 are placed within the retaining carriage. Rods 34 for the retaining carriage can be made of any suitable material, such as plastic, wood, metal, etc., which is capable of supporting the scented media containers 18, 20.

While a preferred form of the invention has been shown in the drawings and described, since variations in the preferred form will be apparent to those skilled in the art, the invention should not be construed as limited to the specific form shown and described, but instead is as set forth in the following claims.

I claim:
1. An air freshening apparatus comprising:
    an outer cylindrical member comprising a first closed end, a second open end, and at least one rectangular shaped longitudinal opening passing through said outer cylindrical member;
    an inner cylindrical member comprising a first closed end, a second open end, and at least one step-shaped longitudinal opening passing through said inner cylindrical member, wherein said inner cylindrical member fits concentrically within said outer cylindrical member forming a frictional interface between said inner and outer cylindrical members, and where said inner cylindrical member is greater in length than said outer cylindrical member such that said open end of said inner cylindrical member extends beyond said open end of said outer cylindrical member;
    at least two replaceable scent filled media containers which are cylindrical in shape and concentrically retained within said inner cylindrical member; and
    means for aligning said at least one step-shaped opening in said inner cylindrical member with said at least one rectangular opening of said outer cylindrical member such that said two replaceable scent filled media containers may be exposed to an air interface either selectively or simultaneously.

2. The apparatus of claim 1, wherein said at least one step-shaped longitudinal opening is defined by three generally rectangular staggered openings adjacent one another in a step formation.

3. The apparatus of claim 1, wherein said at least one step-shaped longitudinal opening is defined by two generally rectangular staggered openings adjacent one another in a step formation.

4. The apparatus of claim 2, further comprising a base member, wherein said base member is attached to said outer cylindrical member.

5. The apparatus of claim 2, further comprising a retaining carriage located within said inner cylindrical member and capable of holding the scent filled media containers, said retaining carriage comprising a first ring member, a second ring member, and at least one rod member, wherein said at least one rod member is connected to said first and second ring members and anchored in said inner cylindrical member.

6. The apparatus of claim 2, wherein said means for aligning said at least one opening of said inner and outer cylindrical members comprises a dial, wherein said dial is attached to said open end of said inner cylindrical member, which extends beyond said outer cylindrical member, to aid in rotating said inner cylindrical member.

* * * * *